US 6,642,726 B2

(12) United States Patent
Weiner et al.

(10) Patent No.: US 6,642,726 B2
(45) Date of Patent: Nov. 4, 2003

(54) APPARATUS AND METHODS FOR RELIABLE AND EFFICIENT DETECTION OF VOLTAGE CONTRAST DEFECTS

(75) Inventors: Kurt H. Weiner, San Jose, CA (US); Gaurav Verma, Atherton, CA (US); Isabella T. Lewis, San Jose, CA (US)

(73) Assignee: KLA-Tencor Corporation, San Jose, CA (US)

( * ) Notice: Subject to any disclaimer, the term of this patent is extended or adjusted under 35 U.S.C. 154(b) by 64 days.

(21) Appl. No.: 10/000,114

(22) Filed: Oct. 30, 2001

(65) Prior Publication Data

US 2003/0001598 A1 Jan. 2, 2003

Related U.S. Application Data

(60) Provisional application No. 60/302,096, filed on Jun. 29, 2001.

(51) Int. Cl.[7] .................... G01R 31/305; G01R 31/00; G01N 23/04; G06K 9/00
(52) U.S. Cl. .................... 324/751; 324/96; 250/311; 250/492.2; 356/456; 382/149
(58) Field of Search ..................... 324/751, 752, 324/753, 501, 96, 765; 250/310, 311, 492.2; 356/237.4, 456; 382/145, 149; 345/617, 618; 438/14, 16

(56) References Cited

U.S. PATENT DOCUMENTS

| | | | | |
|---|---|---|---|---|
| 3,961,190 A | * | 6/1976 | Lukianoff et al. | 250/310 |
| 4,958,373 A | * | 9/1990 | Usami et al. | 382/149 |
| 5,502,306 A | | 3/1996 | Meisburger et al. | 250/310 |
| 5,578,821 A | | 11/1996 | Meisberger et al. | 250/310 |
| 5,592,100 A | * | 1/1997 | Shida et al. | 324/751 |
| 5,665,968 A | | 9/1997 | Meisburger et al. | 250/310 |
| 5,717,204 A | | 2/1998 | Meisburger et al. | 250/310 |
| 5,804,980 A | * | 9/1998 | Nikawa | 324/752 |
| 5,959,459 A | | 9/1999 | Satya et al. | 324/751 |
| 6,038,018 A | | 3/2000 | Yamazaki et al. | 356/237.1 |
| 6,091,249 A | | 7/2000 | Talbot et al. | 324/751 |
| 6,252,412 B1 | | 6/2001 | Talbot et al. | 324/750 |
| 6,344,750 B1 | * | 2/2002 | Lo et al. | 324/751 |

FOREIGN PATENT DOCUMENTS

| EP | 0853243 A2 | 7/1998 | G01R/31/305 |
|---|---|---|---|
| EP | 092275 A2 | 1/1999 | G01R/31/307 |

* cited by examiner

*Primary Examiner*—Anjan K. Deb
(74) *Attorney, Agent, or Firm*—Beyer Weaver & Thomas, LLP

(57) ABSTRACT

Disclosed are methods and apparatus for automatically filtering out physical defects from electrical defects that are found during a voltage contrast inspection of a test structure on a semiconductor device.

21 Claims, 9 Drawing Sheets

APPARATUS AND METHODS FOR RELIABLE AND EFFICIENT DETECTION OF VOLTAGE CONTRAST DEFECTS

CROSS-REFERENCE TO RELATED APPLICATION

This application takes priority under U.S.C. 119(e) of U.S. Provisional Application No.: 60/302,096 filed Jun. 29, 2001 entitled, "APPARATUS AND METHODS RELIABLE AND EFFICIENT DETECTION OF VOLTAGE CONTRAST DEFECTS" by Kurt H. Weiner, Gaurav Verna, and Isabella T. Lewis, which is incorporated by reference in its entirety for all purposes.

BACKGROUND OF THE INVENTION

This invention relates to methods and apparatus for detecting electrical defects in a semiconductor device or test structure having a plurality of features that are specifically designed to produce varying voltage potentials during a voltage contrast inspection. More particularly, it relates to voltage contrast techniques for detecting open and short type defects within the features of the circuit or test structure.

A voltage contrast inspection of a test structure is accomplished with a scanning electron microscope. The voltage contrast technique operates on the basis that potential differences in the various locations of a sample under examination cause differences in secondary electron emission intensities when the sample is the target of an electron beam. The potential state of the scanned area is acquired as a voltage contrast image such that a low potential portion of, for example, a wiring pattern might be displayed as bright (intensity of the secondary electron emission is high) and a high potential portion might be displayed as dark (lower intensity secondary electron emission). Alternatively, the system may be configured such that a low potential portion might be displayed as dark and a high potential portion might be displayed as bright.

A secondary electron detector is used to measure the intensity of the secondary electron emission that originates from the path swept by the scanning electron beam. Images may then be generated from these electron emissions. A defective portion can be identified from the potential state or appearance of the portion under inspection. The portion under inspection is typically designed to produce a particular potential and resulting brightness level in an image during the voltage contrast test. Hence, when the scanned portion's potential and resulting image appearance differs significantly from the expected result, the scanned portion is classified a defect.

Several inventive test structures designed by the present assignee are disclosed in copending U.S. patent application Ser. No. 09/648,093 (Attorney Docket No. KLA1P016A) by Satya et al., filed Aug. 25, 2000, which application is incorporated herein in its entirety. In one embodiment, a test structure is designed to have alternating high and low potential conductive lines during a voltage contrast inspection. In one inspection application, the low potential lines are at ground potential, while the high potential lines are at a floating potential. However, if a line that is meant to remain floating shorts to an adjacent grounded line, both lines will now produce a low potential during a voltage contrast inspection. If there is an open defect present within a line that is supposedly coupled to ground, this open will cause a portion of the line to be left at a floating potential to thereby produce a high potential during the voltage contrast inspection. Both open and short defects causes two adjacent lines to have a same potential during the voltage inspection.

In theory, defects within the above described test structure may be found by comparing images of portions of the test structure that are designed to have identical appearances during voltage contrast inspection. Thus, any difference between two supposedly identical imaged portions can be classified as an electrical defect. However, certain physical defects within the conductive line may introduce "nuisance" defects into the inspection process. That is, physical defects may be inadvertently counted as electrical defects. In one voltage contrast technique, a first set of imaged adjacent conductive lines are subtracted from a second set of imaged adjacent lines. The imaged sets are selected so that they will be identical if they contain no defects. Thus, if the subtraction operation results in a nonzero value, imaged sets are flagged as having one or more defects. Unfortunately, this subtraction procedure may result in physical defects being flagged, as well as electrical defects.

The total defect count which results from a voltage contrast inspection on specially designed test chips can run into the thousands for a complete wafer. Manually reviewing and classifying these defects to isolate the electrical defects from the physical defects is very time consuming and tedious. Additionally, manual classification is inherently subject to human errors.

Accordingly, there is a need for improved apparatus and methods for detecting electrical defects in semiconductor device and test structures without having to manually filter physical defects from the inspection results.

SUMMARY OF THE INVENTION

Accordingly, mechanisms are provided for automatically filtering out physical defects from electrical defects during a voltage contrast inspection of a test structure on a semiconductor device. In general terms, the test structure is designed to include a plurality of features that will charge to specific voltage potentials when scanned with an electron beam during a voltage contrast inspection. Images of the scanned features are generated, and the relative brightness level of each feature depends on the corresponding potential of each feature during the inspection. That is, some features are expected to appear dark, and other features are expected to appear bright. If there is no defect present in the scanned feature, the corresponding image will have the expected number of bright and dark features. However, if there is a defect present, the number of dark and bright features within the generated image will not match expected results.

The test structure may also be designed so have substantially identical pairs of features. In one implementation, each pair includes a feature that is expected to appear bright and another feature that is expected to appear dark within the generated image. Thus, an image may be generated for each set of features. The generated images are then subtracted from each other to determine whether any defects are present. Alternatively, an image of an inspected set of features may be compared to a reference image constructed from a design database. A subtraction that results in a defect is then analyzed to determine whether it is an electrical defect or a physical defect.

In one embodiment, the aspect ratio of each scanned feature is known. If the defect has substantially the same aspect ratio as the known aspect ratio, it is determined to be an electrical defect. Otherwise, it is determined to be a physical defect. Other mechanisms are described for locating the found electrical defect and filtering out the location of physical defects during this process. Additionally, mechanisms are described for calibrating the inspection process based on a test structure having a plurality of known defects.

In one embodiment, a method of detecting defects in a plurality of features on a semiconductor device is disclosed. Each of the features is designed to have a particular potential when scanned with an electron beam. A first and second image of a first and second set of feature portions, respectively, are provided. The first and second images are generated as a result of scanning an electron beam over the first and second set of feature portions, and the first set of feature portions are designed to be substantially identical to the second set of feature portions when there is no defect present. The first image is subtracted from a second image to generate a difference image. When the difference image has a significantly sized defect that represents a difference between the first set of feature portions and the second set of feature portions, it is determined whether the defect is an electrical defect or a physical defect. In one implementation, this determination is accomplished by determining that the defect indicates an electrical defect when the defect has about a same aspect ratio as a one of the scanned feature portions. When the defect has a different aspect ratio than a one of the scanned feature portions, it is determined that the defect indicates a physical defect.

In a specific implementation, the features include a plurality of conductive lines, and the conductive lines are designed to include a plurality of lines at a grounded potential interleaved and are arranged parallel with a plurality of lines at a floating potential. An electrical defect is found when two adjacent conductive lines have a same potential when scanned with the electron beam. In another aspect, the scanned feature portions are a plurality of end stub portions of the conductive lines, and each end stub portion has a substantially same aspect ratio.

In a further implementation, it is determined that the electrical defect is a short when the when the defect has a first brightness value. It is determined that the electrical defect is an open when the differ when the defect has a second brightness value. In one aspect, the first brightness value is higher than the second brightness value. In yet another embodiment, when an electrical defect is found, the electron beam is then scanned along the defective feature perpendicular to the first scan to form a plurality of images of portions of the defective feature not scanned in the first scan and one or more features adjacent to the defective feature. A first image of the defective feature is subtracted from a second image of the defective feature to obtain a difference image. The defective feature is designed to have a first portion having a bright appearance and a second portion having a dark appearance when there is an open defect present within the defective feature. When the difference image has a significantly sized second defect that represents a difference between the first and second image of the defective feature, it is then determined whether the second defect represents a location of the electrical defect or a physical defect.

In a preferred implementation, determining whether the second defect represents a location of the electrical defect or a physical defect is accomplished by determining that the second defect represents a location of the electrical defect and that the electrical defect is an open when the second defect would be adjacent to a dark and bright portion of the defective feature if the difference image were overlaid with the first or second image. It is determined that the second defect represents a location of the electrical defect and that the electrical defect is a short defect when the second defect would not be adjacent to a dark and bright portion of the defective feature and the second defect touches two adjacent features if the difference image were overlaid with the first or second image. It is determined that the second defect represents a location of a physical defect when the second defect would not be adjacent to a dark and bright portion of the defective feature and the second defect does not touch two adjacent features if the difference image were overlaid with the first or second image.

In another aspect, the invention pertains to a computer program product for detecting defects in a plurality of features on a semiconductor device. Each of the features is designed to have a particular potential when scanned with an electron beam, the computer program product includes at least one computer readable medium and computer program instructions stored within the at least one computer readable product configured to cause the inspection system to perform one or more of the above described methods.

In another aspect, the invention pertains to an inspection system for detecting defects in a plurality of features on a semiconductor device. Each of the features is designed to have a particular potential when scanned with an electron beam. The system includes a beam generator for generating an electron beam, a detector for detecting electrons, and a controller arranged to cause the beam generator to scan an electron beam over a first and a second set of feature portions. The first set is designed be substantially identical to the second set of feature portions when there is no defect present. The controller is further arranged to generate a first image of the first set of feature portions and a second image of the second set of feature portions from electrons detected by the detector emitted from the scanned feature portions in response to the scanned electron beam. The controller is also configured to subtract the first image from the second image to generate a difference image.

When the difference image has a significantly sized defect that represents a difference between the first set of feature portions and the second set of feature portions and the defect has about a same aspect ratio as a one of the scanned feature portions, the controller is further configured to determine that the defect indicates an electrical defect within the scanned features. When the difference image has a significantly sized defect that represents a difference between the first set of feature portions and the second set of feature portions and the defect has a different aspect ratio than a one of the scanned feature portions, the controller is further configured to determine that the defect indicates a physical defect.

These and other features and advantages of the present invention will be presented in more detail in the following specification of the invention and the accompanying figures which illustrate by way of example the principles of the invention.

DETAILED DESCRIPTION OF SPECIFIC EMBODIMENTS

Reference will now be made in detail to a specific embodiment of the invention. An example of this embodiment is illustrated in the accompanying drawings. While the invention will be described in conjunction with this specific embodiment, it will be understood that it is not intended to limit the invention to one embodiment. On the contrary, it is intended to cover alternatives, modifications, and equivalents as may be included within the spirit and scope of the invention as defined by the appended claims. In the following description, numerous specific details are set forth in order to provide a thorough understanding of the present invention. The present invention may be practiced without some or all of these specific details. In other instances, well known process operations have not been described in detail in order not to unnecessarily obscure the present invention.

The detection techniques of the present invention may be applied to any type of structure having features that respond to a voltage contrast inspection in a known way when defects are not present within the test structure. The test structure include features that will have particular voltage potentials when scanned with an electron beam. Some of the features may retain a low potential, while other features charge up to a higher potential. When an image is generated from electrons emitted from the scanned features, the image will also depend on the features' particular potentials achieved or retained during the electron beam scan. For example, a features having a low potential may result in a bright feature, while a feature with a high potential may result in a dark feature within the image. Alternatively, low potential features may appear dark, and high potential features appear bright.

Since the test structure is designed to result in a particular image, one may determine whether there is a defect in a portion of the test structure by comparing the imaged "target" portion to a reference image having no defects. The reference image may be an identical portion of the test structure or may be generated from a design database (e.g., that was used to fabricate the test structure). Significant differences between the target and the reference images may be classified as defects. The present invention includes mechanisms for analyzing these defects to determine whether they are electrical or physical defects.

Figure 1:
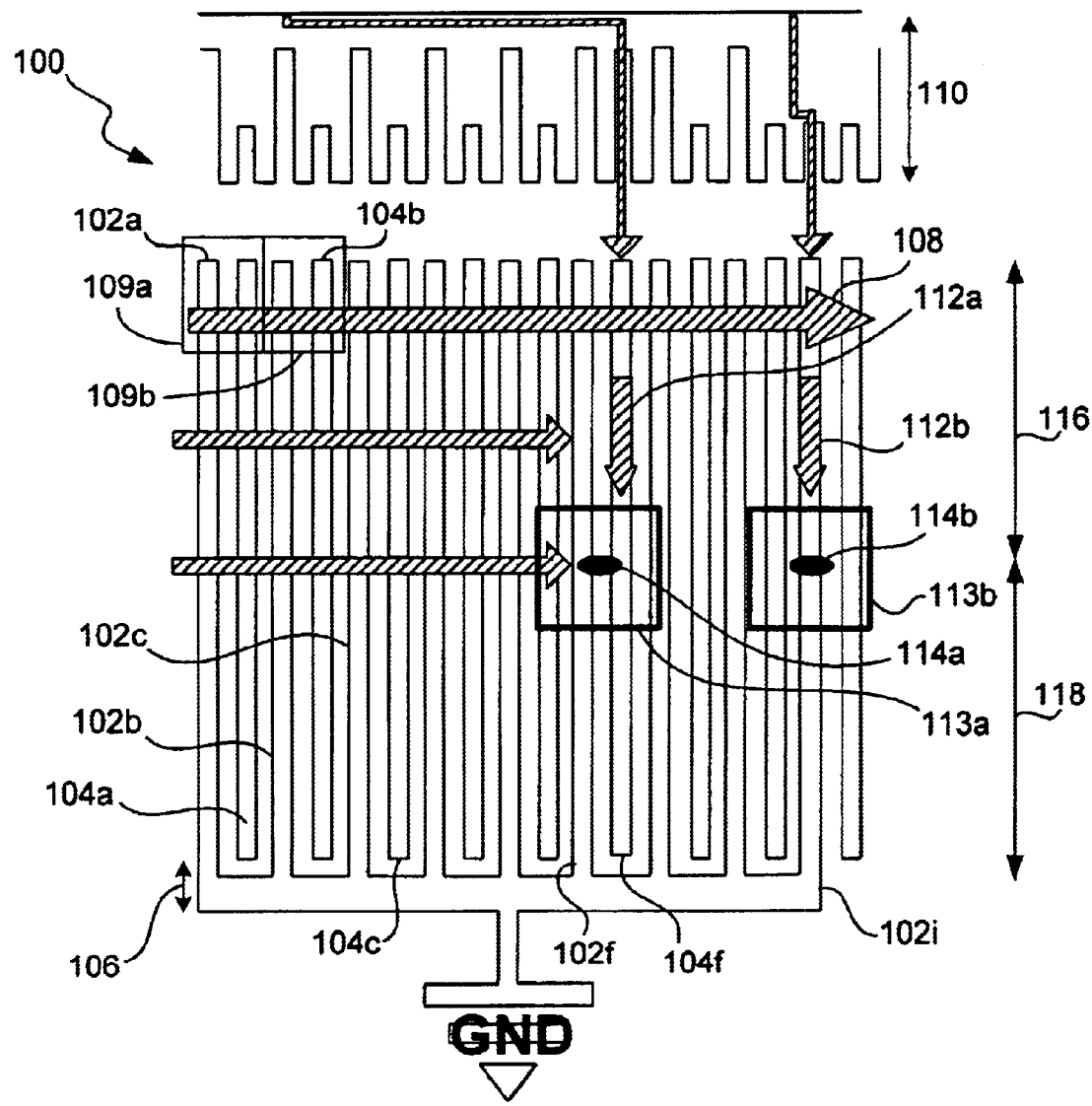
FIG. 1 is a diagrammatic top view representation of a test structure on which the techniques of the present invention may be implemented in accordance with one embodiment of the present invention.

FIG. 1 is a diagrammatic top view representation of a test structure 100 on which the techniques of the present invention may be implemented in accordance with one embodiment of the present invention. Test structure 100 is referred to as a comb-like structure. As shown, the test structure 100 includes a plurality of grounded conductive lines and a plurality of floating conductive line 104. Voltage contrast images of a top portion of the conductive lines 102 and 104 are generated as an electron beam moves in direction 108. Each image is referred herein to as a "cell."

Preferably, the image cells correspond to feature portions that are designed to result in substantially identical images when no defects are present. In one embodiment, an image cell is generated for a top portion of each pair of grounded and floating lines. However, other portions of the features (e.g., a middle portion of the conductive lines) may be scanned. As shown, when the conductive lines are scanned in direction 108, cell 109a is first obtained and then cell 109b is obtained. Since the test structure 100 is expected to have alternating lines of grounded and floating potential, each image cell is expected to contain a bright line and a dark line. For example, the grounded lines 102 will appear bright, while the floating lines 104 will appear dark. Of course, the inspection tool may be set up so that the grounded lines 102 appear dark and the floating lines 104 appear bright. The intensity value of the conductive lines as the electron beam scans across them may also be graphed as shown in intensity graph 110. When there are no defects, the intensity values are expected to include alternating high and low intensity values.

However, the test structure may contain electrical defects, as well as physical defects. As shown, there is an electrical short 114a between line 102f and 104f. This short 114a causes both lines 102f and 104f to appear bright. Another type of electrical defect that may occur in the test structure 100 is an open. As shown, there is an open defect 114b in line 102i. An open defect causes a portion 116 of line 102i to have a floating potential. Accordingly, the floating portion 116 will appear dark, while the portion of the line that remains coupled to ground (118) will have a bright appearance.

In sum, when two lines are shorted together, both lines will appear bright when scanned in direction 108. In contrast, when a supposedly grounded line contains an open, the top portion 116 of such line has the same dark appearance as its neighboring floating conductive lines when scanned in direction 108. Accordingly, when the electron beam moves in direction 108, a defect may be found when a particular cell is subtracted from another cell. For example, cell 109b may be subtracted from cell 109a. If the particular cell does not have a defect, this subtraction will ideally produce zero results. In contrast, when the particular cell has a defect, this subtraction will produce a significant difference that is then classified as a defect. Electron beam tool parameter settings determine the percentage difference between the two cells that will be classified as a defect. The parameter settings may be experimentally determined and adjusted, for example, according to techniques described below with reference to FIG. 6.

Figure 2:
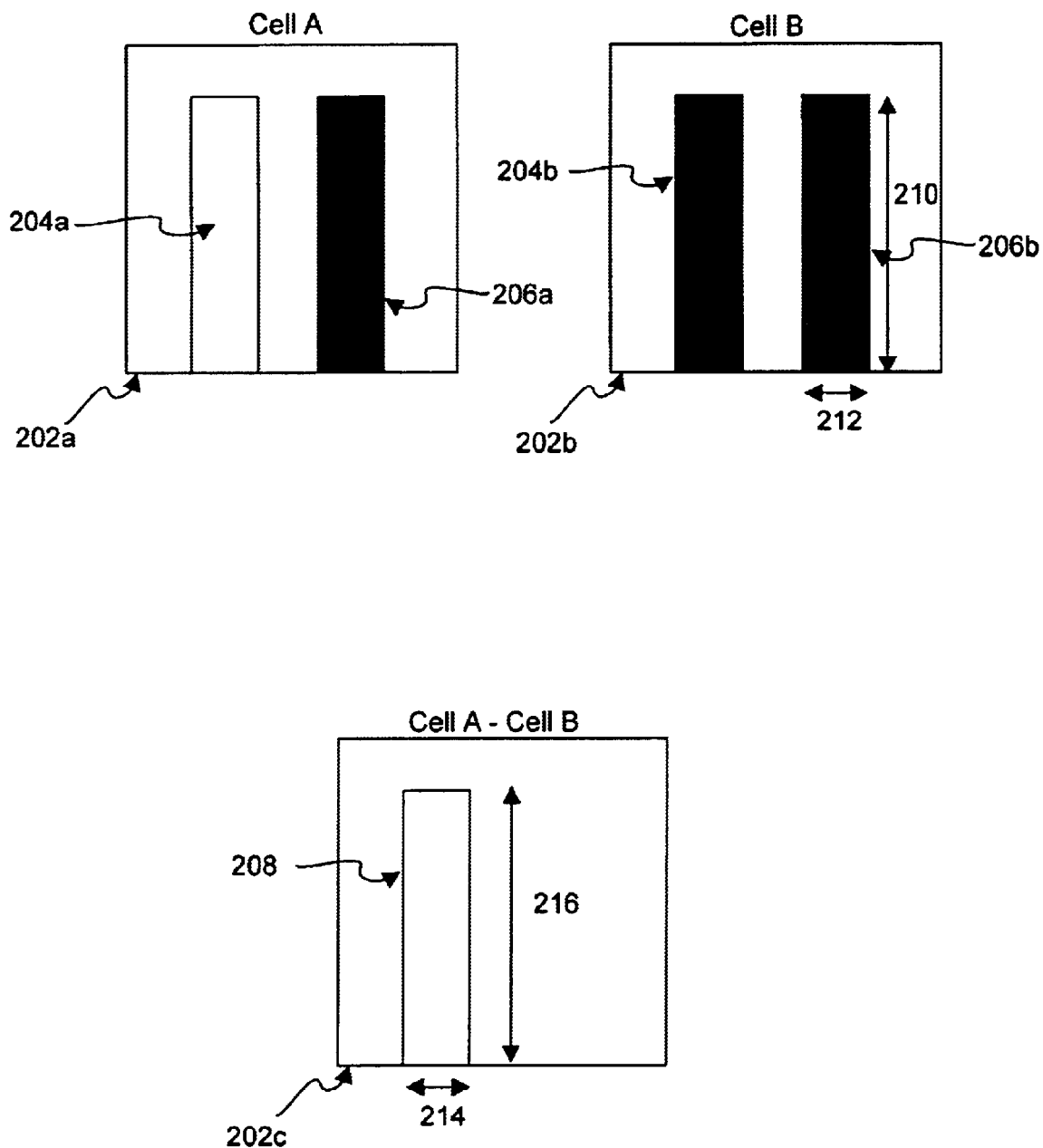
FIG. 2 is a diagrammatic representation of a cell subtraction procedure, wherein one of the cells contains an electrical defect, in accordance with one embodiment of the present invention.

FIG. 2 illustrated a cell subtraction procedure, wherein one of the cells contains an electrical defect, in accordance with one embodiment of the present invention. As shown, cell 202a contains a pair of conductive line portions 204a and 206a with different brightness levels (e.g., cell 204a is bright and cell 206a is dark). Cell 202b contains two conductive line portions 204b and 206b having the same brightness level (e.g., they both appear dark). Since each cell is expected to have conductive line portions with different brightness levels, a cell that has conductive lines with the same brightness level is expected to represent a defective feature. As shown, cell 202a is defect free, while cell 202b contains defective conductive line 204b. If the above described comb type test structure 100 is being imaged, conductive line 204b probably contains an open. If there was an electrical short present, both lines within the cell would appear bright in this implementation.

An electrical defect may be found by subtracting two cells. Cell 202c contains a representation of a result from subtracting cell 202b from cell 202a. The result of this subtraction is defect 208. Defect 208 is substantially the same size as a scanned feature portion. Defect 208 has width 214 and height 216, which are substantially equal to feature width 212 and height 210. This similarity may be used to distinguish electrical defects from physical defects, as explained further below.

Figure 3:
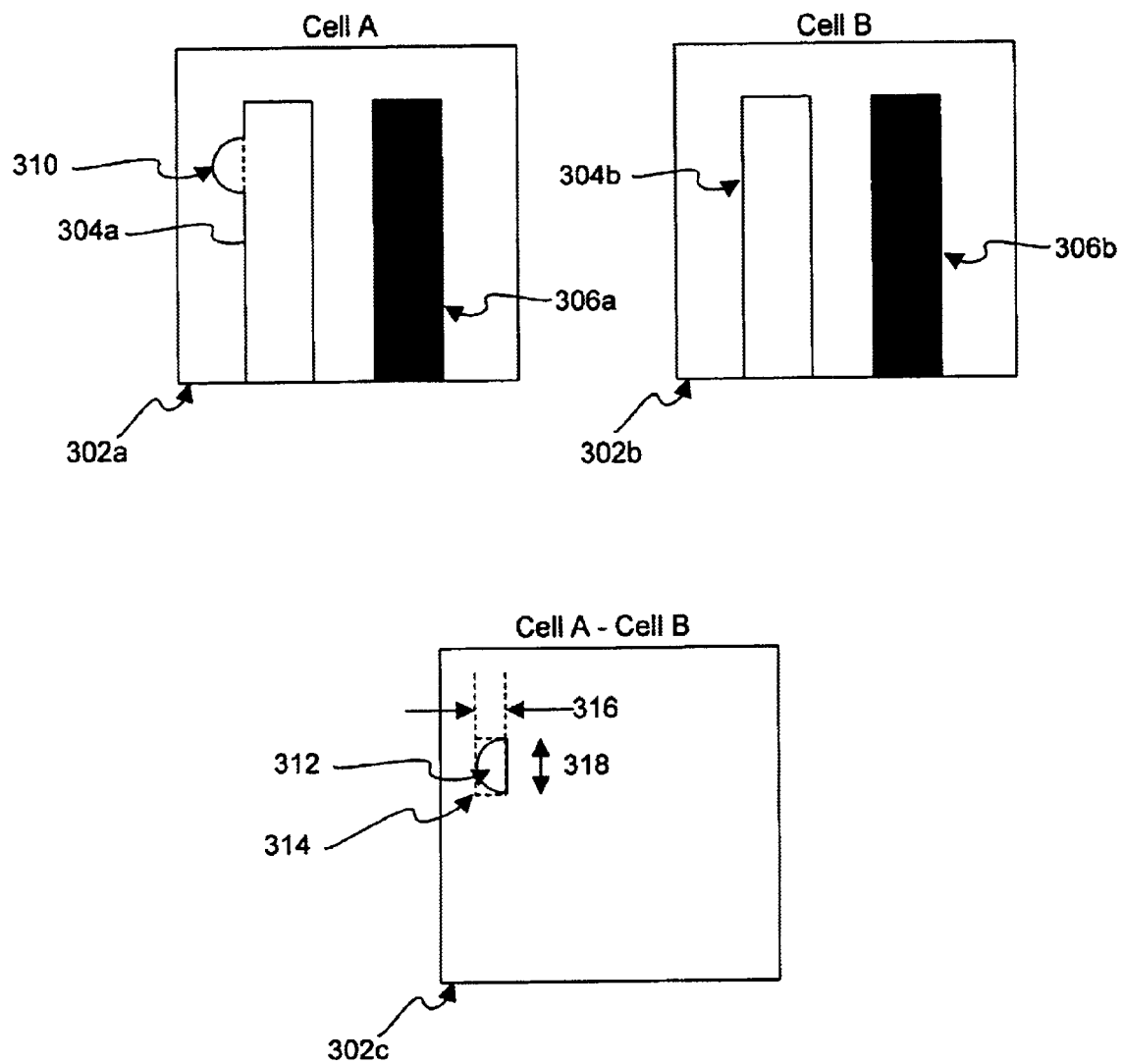
FIG. 3 illustrates subtraction process for cells, wherein one of the cells contains a physical defect, in accordance with one embodiment of the present invention.

FIG. 3 illustrates a subtraction procedure using two cells, wherein one of the cells contains a physical defect 310, in accordance with one embodiment of the present invention. As shown, cell 302a includes bright line 304a and dark line 306a. Cell A also includes a physical defect 310. Cell 302b contains bright line 304b and dark line 306b. Since each cell contains both a dark line and a bright line, the corresponding features of such cells do not contain electrical defects. However, the above described subtraction method may result in a defect being found. As illustrated, the results of such subtraction process are represented in cell 302c, where cell 302b is subtracted from cell 302a. As shown, this subtraction process results in defect 312.

The present invention includes techniques for filtering out physical defects (e.g., 312 of FIG. 3) from electrical defects. The physical defects may take any form, such as bumps along the edge of the line, indentations along the edge of the line, or holes within the center of the line. Electrical defects may be distinguished from physical defects since the aspect ratio of an electrical defect will tend to have about the same aspect ratio as a corresponding scanned feature portion. As shown in FIG. 2, the aspect ratio for feature portion 206b (the scanned top portion is herein referred to as a "stub") has length 210 and width 212, which are substantially the same as the aspect ratio of electrical defect 208 having length 216 and width 214. In one particular design process, each stub has a length of five μm and a width of 0.13 μm. In contrast, a physical defect will have a significantly different aspect ratio than a scanned feature portion (e.g., stub). As shown in FIG. 3, physical defect 312 has an aspect ratio with a length 318 and a width 316 which vary significantly from the width and length of a scanned stub (as shown in FIG. 2). Accordingly, when the defect has an aspect ratio that is substantially the same as a scanned feature portion's aspect ratio, the defect is classified as an electrical defect.

Figure 4:
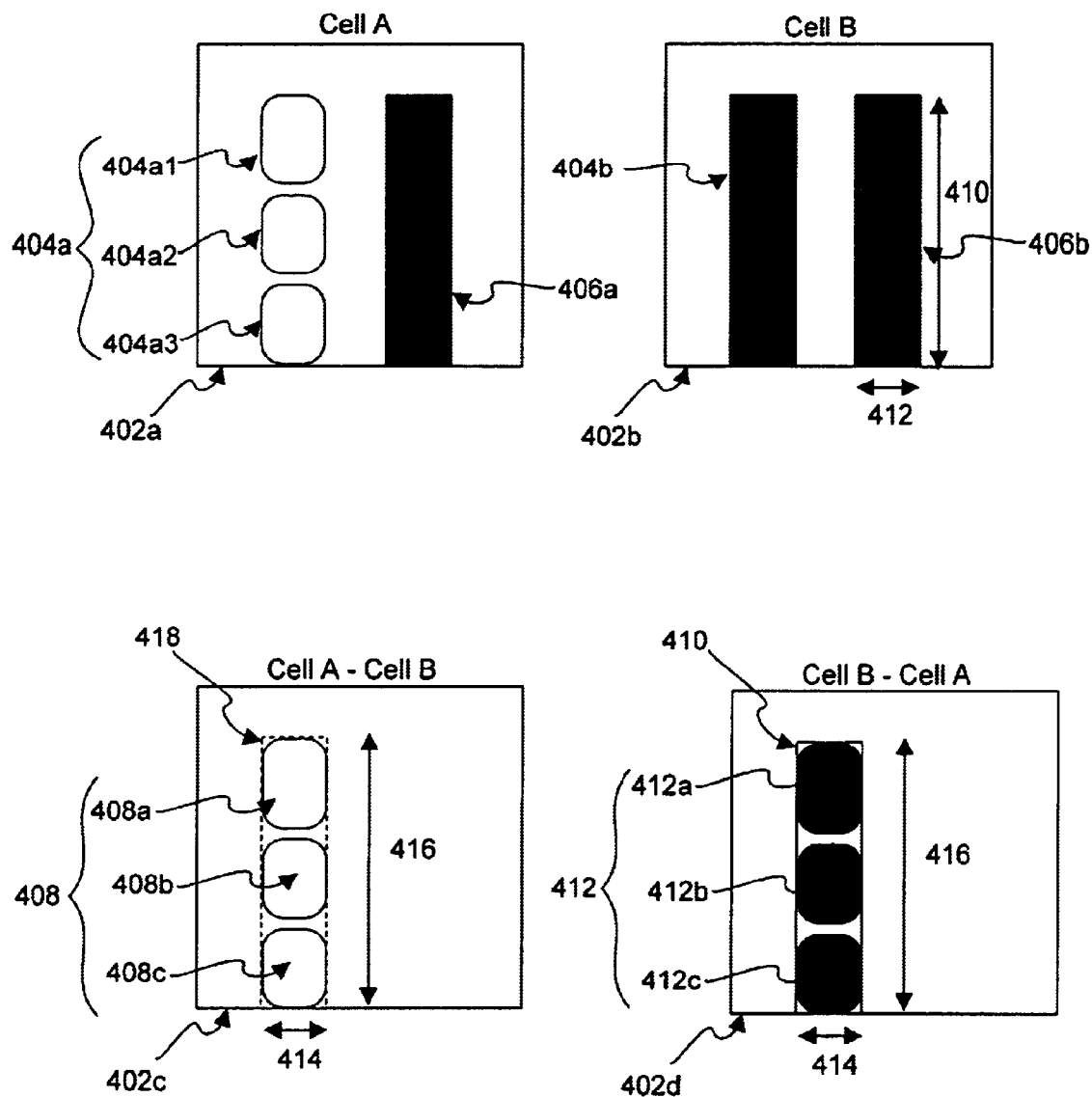
FIG. 4 is a diagrammatic illustration of a subtraction procedure implemented on a cell containing a partially imaged stub in accordance with one embodiment of the present invention.

Even when the stubs are not properly imaged, the techniques of the present invention may provide effective mechanisms for filtering out physical defects from electrical defects. FIG. 4 is a diagrammatic illustration of a subtraction procedure implemented on cells containing a partially imaged stub in accordance with one embodiment of the present invention. As shown, cell 402a contains a partially imaged stub 404a. However, this partially imaged stub 404a has an intensity value that contrasts with the adjacent stub 406a. Accordingly, this cell does not contain a defect. Cell 402b includes two dark stubs 404b and 406b. Since stubs 404b and 406b are both dark, cell 402b is associated with an electrical defect.

Cell 402c represents subtraction of cell 402b from cell 402a. As shown, the aspect ratio for defect 408 may be determined by drawing a boundary 418 around the resulting defects 408a, 408b, and 408c. This boundary 418 has a length 416 and a width 414. This length 416 and width 414 of defect 408 is substantially equivalent to the aspect ratio of one of the stubs as shown in cell 402b having length 410 and width 412. The resulting defect will have the same aspect ratio when cell 402a is subtracted from cell 402b, as compared to subtracting cell 402b from cell 402a. Cell 402d illustrates defect 410 having dark spots 412a, 412b, and 412c resulting from such alternative subtraction process. As shown, this defect 412 has the same aspect ratio having length 416 and width 414 as the defect 408 in cell 402c. Thus, both defects 408 and 412 are classified as electrical defects since their aspect ratios are substantially the same as the aspect ratio of a scanned stub.

Figure 5A:
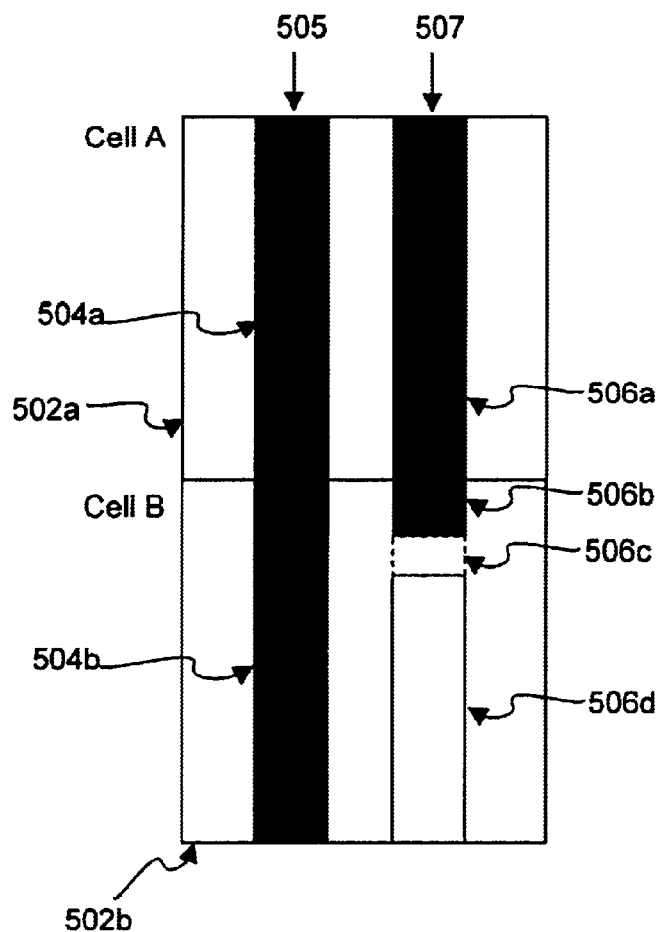
FIG. 5A illustrates a technique for determining the location of an open defect within two or more electrically defective test features in accordance with one embodiment of the present invention.
Figure 5A:
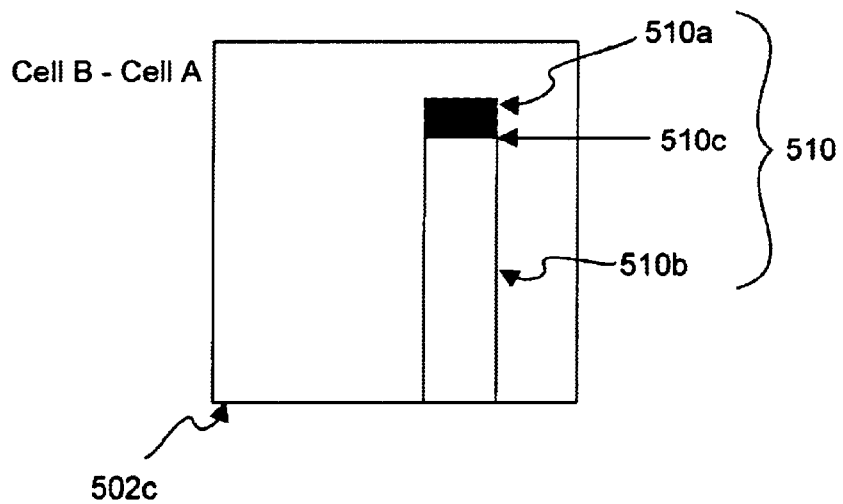

As illustrated in FIG. 1, when it is determined that a conductive line contains an electrical defect by scanning in direction 108, the actual defect (e.g., short or open) may be located by scanning in direction 112. While searching for an electrical defect, a physical defect may also be found. Preferably, the location of physical defects are filtered out from the location of an electrical defect. FIG. 5A illustrates a technique for determining the location of an open type defect in accordance with one embodiment of the present invention. As the electron beam scans down the defective conductive line (as illustrated by direction 112b of FIG. 1), cell images are generated for portions of the defective conductive line, as well as portions of adjacent conductive lines. Any suitable number of lines may be imaged during this scan. For simplicity, only two lines are shown in FIG. 5A.

Cells 502a and 502b illustrate contiguous portions of two conductive lines 505 and 507. In cell 502a, the first conductive line 505 contains a dark portion 504a, and the second conductive line 507 contains a dark portion 506a. In cell 502b, the first conductive line includes a dark line portion 504b which is contiguous to the dark portion 505a of cell 502a. In cell 502b, the second conductive line includes a dark line portion 506b, the electrical open 508c, and a bright line portion 506d.

Cell 502c illustrates the results from subtracting cell 502a from cell 502b. Preferably contiguous cells are subtracted from each other. However, non-contiguous cells may also be subtracted from each other. The subtraction produces dark portion 510a and bright portion 510b. It is determined that the defect is an electrical defect when there is a transition 510c between dark and bright intensity within the resulting defects 510. The transition 510c location may be determined to be the defect location. Alternatively, the defect portion 510a that is positioned above the intensity transition 510c may be determined to be the defect location. This location of defect 510a corresponds more accurately to the actual electrical defect location.

Figure 5B:
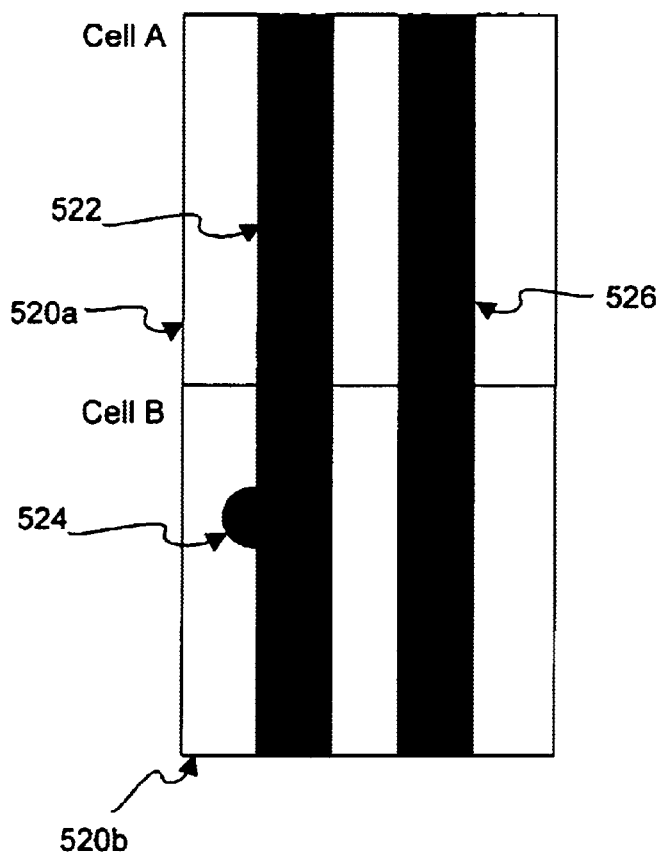
FIG. 5B illustrates a subtraction process for determining the location of an open type electrical defect within two or more electrically defective test features while filtering out the locations of any physical defect in accordance with one embodiment of the present invention.
Figure 5B:
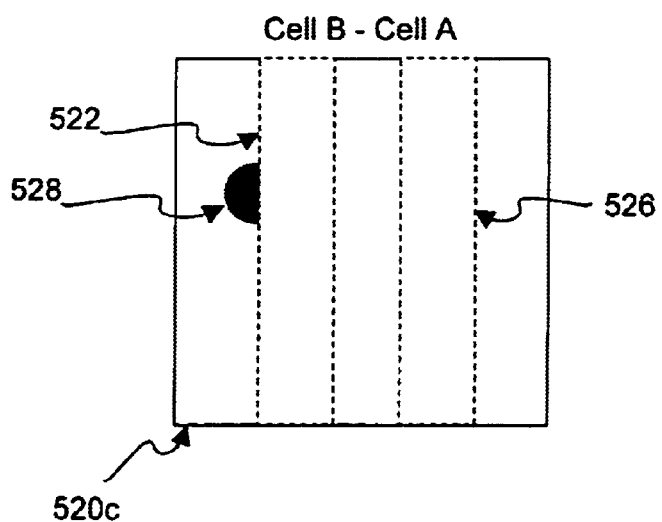

FIG. 5B illustrates a subtraction process for determining the location of an open type electrical defect within two or more electrically defective test features while filtering out the locations of any physical defect in accordance with one embodiment of the present invention. Portions of two dark lines 522 and 526 are present in cell 520a and cell 520b. However, cell 520b also contains physical defect 524. A physical defect may be encountered as the electron beam scans down the defective line before reaching the actual electrical defect. In this case, since the electrical defect is an open defect, both lines 522 and 526 appear dark. In other imaging implementations, both lines may appear bright for an open type defect before reaching the open defect.

Cell 520c illustrates the subtraction of cell 520a from cell 520b. As shown, the subtraction results in defect 528.

However in this case, there is no transition in intensity adjacent to the defect 528 (as when the actual electrical open defect is found). Thus, it is determined that this defect 528 is a physical defect, as opposed to an electrical defect. Alternatively, since the position of the actual electrical defect is expected to be within area 522 or area 526, if the defect is not within these areas 522 or 526 it may be classified as a physical defect. If the difference cell 520c was overlaid with the non-defective cell 520a, these areas correspond to the conductive line portions 522 and 526. However, this alternative technique may not work for other types of defects such as indentations or holes.

Figure 5C:
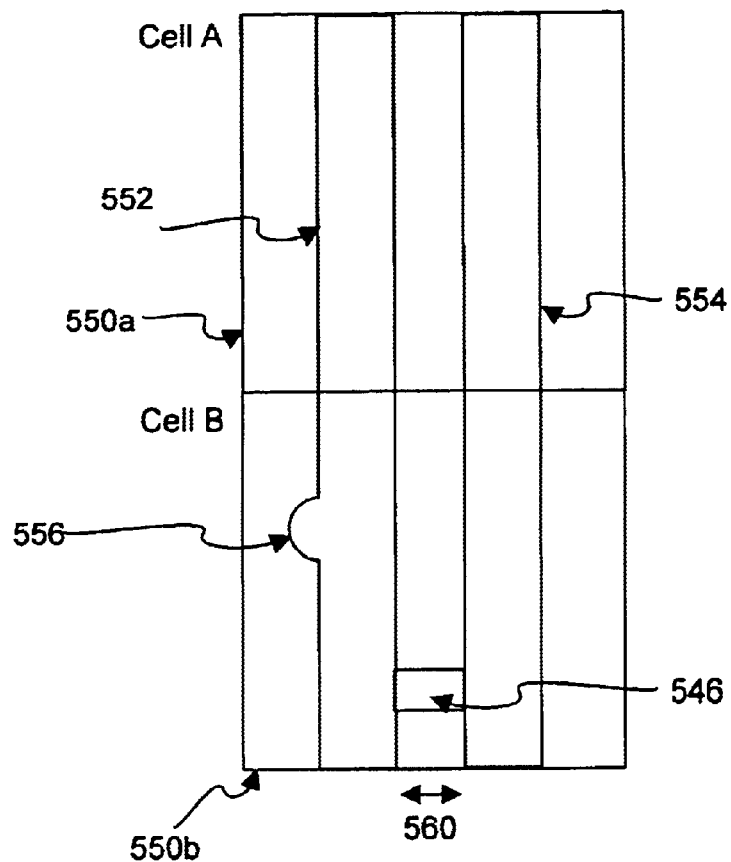
FIG. 5C illustrates a subtraction process for determining the location of a short type electrical defect within two or more electrically defective test features while filtering out the locations of any physical defect in accordance with one embodiment of the present invention.
Figure 5C:
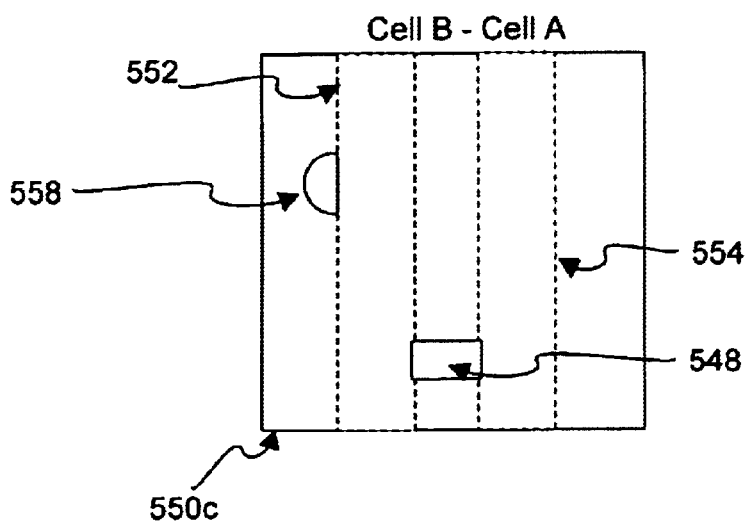

Another type of electrical defect is a short. Such a defect is illustrated in FIG. 1 as defect 114a. In one short defect example, as the electron beam scans down a defective line and its adjacent lines to find a short's location, the defective line and the adjacent lines are expected to have a same intensity value. As shown in FIG. 5C, cell 550a and cell 550b contains bright lines 552 and 554. Cell 550b also includes a physical defect 556 and a short defect 557. Cell 550c illustrates the results from subtracting cell 550a from cell 550b. This subtraction results in physical defect 558 and short defect 559.

Any suitable technique may be utilized to distinguish the electrical defect 559 from the physical defect 558. Initially, the areas of the conductive lines may be determined. As shown, cell 550c includes area 552 and area 554. In one technique, the defect image 550c may be overlaid with the image 550a which contains no defects to determine conductive line areas 552 and 554 in the defect image 550c. A short type defect would be expected to touch both areas 552 and 554. Accordingly, since defect 559 touches area 552 and area 554, it is determined to be an electrical defect. In contrast, if the defect merely touches one of the areas, the defect is determined to be a physical defect. Since defect 558 merely touches area 552 and not area 554, it is determined to be a physical defect. Alternatively, it may determined whether the defect has a substantially same width as the spacing between each scanned feature (e.g., 560). If the defect width is substantially the same, it is classified as an electrical short defect. If the defect width is not substantially the same, it is classified as a physical defect. If a particular defect is classified as an electrical defect, its location is determined to be the location for the short defect.

Figure 6:
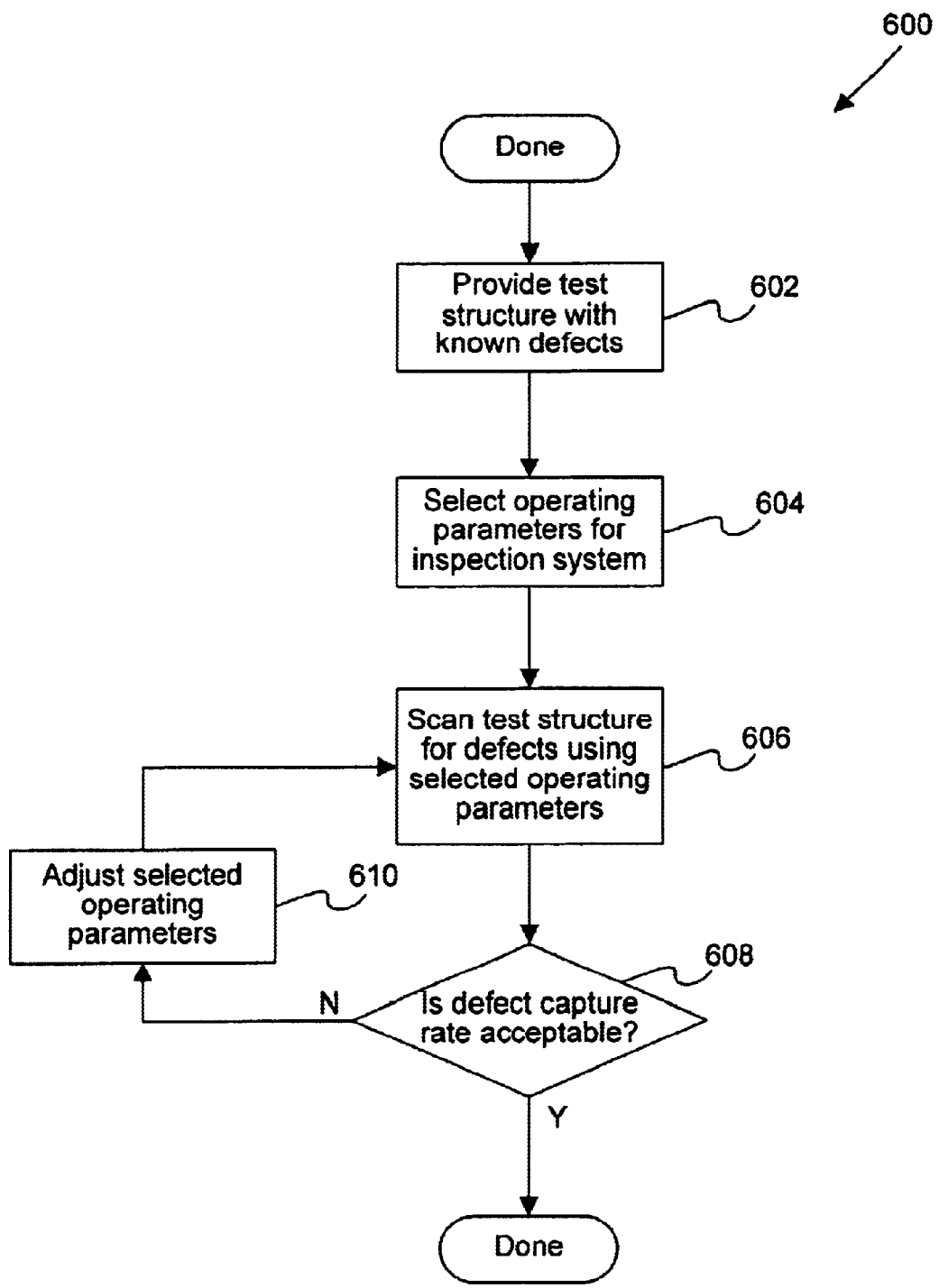
FIG. 6 is a flowchart illustrating a calibration procedure in accordance with one embodiment of the present invention.

Mechanisms for calibrating the inspection tool may also be implemented. FIG. 6 is a flowchart illustrating a calibration procedure in accordance with one embodiment of the present invention. Initially, a test structure having a plurality of known defects is provided in operation 602. For example, the test structure is a comb type structure that includes a plurality of known opens and short defects. Additionally, the test structure may include a number of known physical defects. Operating parameters for the inspection system (e.g., scanning electron microscope) are then selected in operation 604. Operating parameters include, but are not limited to, landing energy (for the electron beam), extraction energy, acceleration voltage, sensitivity, threshold, etc. The operating parameters may also include the specific algorithms used to filter out physical defects from electrical defects.

The test structure is then scanned for defects using the selected operating parameters in operation 606. It is then determined whether the defect capture rate is acceptable in operation 608. For example, it may determined whether all or a significant portion (greater than 95%) of the known electrical defects have been captured. Additionally, it may be determined whether the physical defects were filtered out of the defect captures. If the capture rate is acceptable, the procedure 600 ends. If the defect capture rate is not acceptable, the selected operating parameters are then adjusted in operation 610. For example, the settings of the scanning electron microscope that affect defect detection sensitivity are adjusted. Additionally, the techniques for distinguishing between electrical and physical defects may be modified if the electrical defects are not being properly distinguished from the physical defects. The test structure continues to be scanned for defects and the selected operating parameters adjusted until the defect capture rate is within acceptable limits.

These known defects may also be used for in-situ monitoring the performance of the inspection. For every wafer that is scanned, statistics are automatically maintained regarding the capture rate of the known defects. These statistics provide the ability to monitor the performance of the tool for every inspection. If the performance of the inspection degrades, this can be determined in real time and the operator can be alerted. The operator can then re-optimize the electron microscope parameters to obtain acceptable capture rates.

Figure 7:
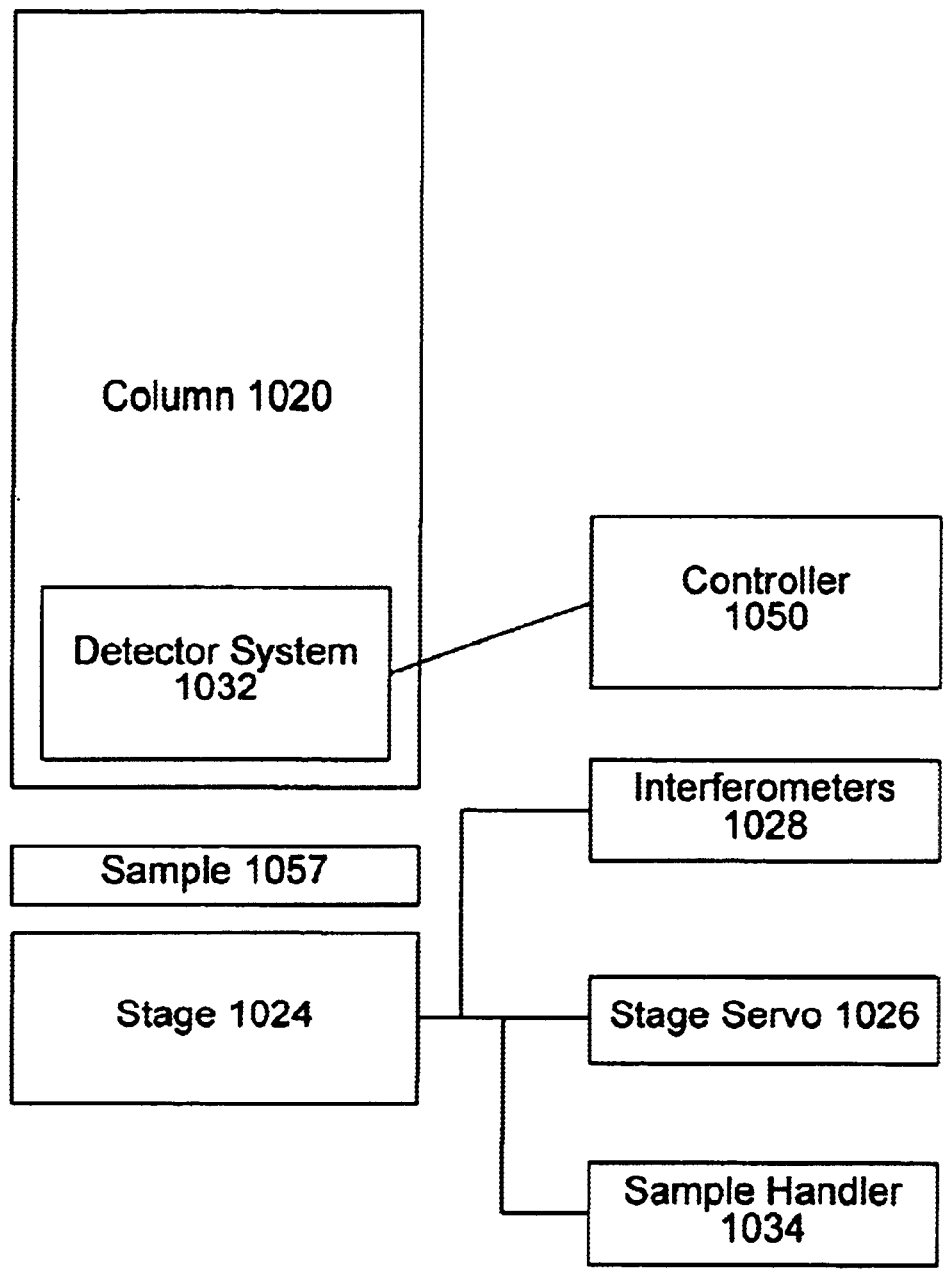
FIG. 7 is a diagrammatic representation of a system in which the techniques of the present invention may be implemented.

FIG. 7 is a diagrammatic representation of a scanning electron microscope (SEM) system in which the techniques of the present invention may be implemented. The detail in FIG. 7 is provided for illustrative purposes. One skilled in the art would understand that variations to the system shown in FIG. 7 fall within the scope of the present invention. For example, FIG. 7 shows the operation of a particle beam with a continuously moving stage. However, the test structures and product structures and many of the inspection techniques described herein are also useful in the context of other testing devices, including particle beams operated in step and repeat mode. As an alternative to moving the stage with respect to the beam, the beam may be moved by deflecting the field of view with an electromagnetic lens. Alternatively, the beam column to be moved with respect to the stage.

Sample 1057 can be secured automatically beneath a particle beam 1020. The particle beam 1020 can be a particle beam such as an electron beam. The sample handler 1034 can be configured to automatically orient the sample on stage 1024. The stage 1024 can be configured to have six degrees of freedom including movement and rotation along the x-axis, y-axis, and z-axis. In a preferred embodiment, the stage 1024 is aligned relative to the particle beam 1020 so that the x-directional motion of the stage is corresponds to an axis that is perpendicular to a longitudinal axis of inspected conductive lines. Fine alignment of the sample can be achieved automatically or with the assistance of a system operator. The position and movement of stage 1024 during the analysis of sample 1057 can be controlled by stage servo 1026 and interferometers 1028.

While the stage 1024 is moving in the x-direction, the inducer 1020 can be repeatedly deflected back and forth in the y direction. According to various embodiments, the inducer 1020 is moving back and forth at approximately 100 kHz. According to a preferred embodiment, the stage 1024 is grounded to thereby ground the substrate and any structure tied to the substrate (e.g., source and drains) to allow voltage contrast between the floating and grounded structures as the result of scanning the targeted features.

A detector 1032 can also be aligned alongside the particle beam 1020 to allow further defect detection capabilities. The detector 1032 as well as other elements can be controlled using a controller 1050. Controller 1050 may include a variety of processors, storage elements, and input and output devices. The controller may be configured to implement the defect detection and location and calibration techniques of the present invention. The controller may also be configured to correlate the coordinates of the electron beam with respect to the sample with coordinates on the sample to thereby determine, for example, a location of a determined electrical defect. In one embodiment, the controller is a computer system having a processor and one or more memory devices.

Regardless of the controller's configuration, it may employ one or more memories or memory modules configured to store data, program instructions for the general-purpose inspection operations and/or the inventive techniques described herein. The program instructions may control the operation of an operating system and/or one or more applications, for example. The memory or memories may also be configured to store images of scanned samples, reference images, defect classification and position data, as well as values for particular operating parameters of the inspection system.

Because such information and program instructions may be employed to implement the systems/methods described herein, the present invention relates to machine readable media that include program instructions, state information, etc. for performing various operations described herein. Examples of machine-readable media include, but are not limited to, magnetic media such as hard disks, floppy disks, and magnetic tape; optical media such as CD-ROM disks; magneto-optical media such as floptical disks; and hardware devices that are specially configured to store and perform program instructions, such as read-only memory devices (ROM) and random access memory (RAM). The invention may also be embodied in a carrier wave travelling over an appropriate medium such as airwaves, optical lines, electric lines, etc. Examples of program instructions include both machine code, such as produced by a compiler, and files containing higher level code that may be executed by the computer using an interpreter.

Although the foregoing invention has been described in some detail for purposes of clarity of understanding, it will be apparent that certain changes and modifications may be practiced within the scope of the appended claims. Therefore, the described embodiments should be taken as illustrative and not restrictive, and the invention should not be limited to the details given herein but should be defined by the following claims and their full scope of equivalents.

What is claimed is:

1. A method of detecting defects in a plurality of features on a semiconductor device, each of the features being designed to have a particular potential when scanned with an electron beam, the method comprising:

providing a first and second image of a first and second set of feature portions, respectively, generated as a result of scanning an electron beam over the first and second set of feature portions, wherein the first set of feature portions are designed to be substantially identical to the second set of feature portions when there is no defect present;

subtracting the first image from a second image to generate a difference image; and when the difference image has a significantly sized defect that represents a difference between the first set of feature portions and the second set of feature portions, distinguishing between an electrical defect and a physical defect as being the defect.

2. A method as recited in claim 1, wherein determining whether the defect is an electrical or physical defect is accomplished by:

determining that the defect indicates an electrical defect when the defect has about a same aspect ratio as a one of the scanned feature portions, and determining that the difference feature indicates a physical defect when the defect has a different aspect ratio than a one of the scanned feature portions.

3. A method as recited in claim 1, wherein the features include a plurality of conductive lines and the conductive lines are designed to include a plurality of lines at a grounded potential interleaved and are arranged parallel with a plurality of lines at a floating potential.

4. A method as recited in claim 3, wherein an electrical defect is found when two adjacent conductive lines have a same potential when scanned with the electron beam.

5. A method as recited in claim 4, wherein the scanned feature portions are a plurality of end stub portions of the conductive lines.

6. A method as recited in claim 5, wherein each end stub portion has a substantially same aspect ratio.

7. A method as recited in claim 1, further comprising:

determining that the electrical defect is a short when the defect has a first brightness value; and determining that the electrical defect is an open when the defect has a second brightness value.

8. A method as recited in claim 7, wherein the first brightness value is higher than the second brightness value.

9. A method as recited in claim 7, further comprising:

when an electrical defect is found, scanning the electron beam along the defective feature perpendicular to the first scan to form a plurality of images of portions of the defective feature not scanned in the first scan and one or more features adjacent to the defective feature;

subtracting a first image of the defective feature from a second image of the defective feature to obtain a difference image, wherein the defective feature is designed to have a first portion having a bright appearance and a second portion having a dark appearance when there is an open defect present within the defective feature;

when the difference image of the defective feature has a significantly sized second defect that represents a difference between the first and second image of the defective feature, determining whether the second defect represents a location of the electrical defect or a physical defect.

10. A method as recited in claim 9, wherein determining whether the second defect represents a location of the electrical defect or a physical defect is accomplished by:

determining that the second defect represents a location of the electrical defect and that the electrical defect is an open when the second defect would be adjacent to a dark and bright portion of the defective feature if the difference image were overlaid with the first or second image;

determining that the second defect represents a location of the electrical defect and that the electrical defect is a short defect when the second defect would not be adjacent to a dark and bright portion of the defective feature and the second defect touches two adjacent features if the difference image were overlaid with the first or second image; and determining that the second defect represents a location of a physical defect when the second defect would not be adjacent to a dark and bright portion of the defective feature and the second defect does not touch two adjacent features if the difference image were overlaid with the first or second image.

11. A method as recited in claim 1, wherein the physical defect is selected from a group consisting of a bump in a feature edge, an uneven feature edge, an indentation in a feature edge, and a hole within an interior of the feature.

12. An inspection system for detecting defects in a plurality of features on a semiconductor device, each of the features being designed to have a particular potential when scanned with an electron beam, the system comprising:

beam generator for generating an electron beam;

a detector for detecting electrons; and a controller arranged to:

cause the beam generator to scan an electron beam over a first and a second set of feature portions, wherein the first set is designed be substantially identical to the second set of feature portions when there is no defect present;

generate a first image of the first set of feature portions and a second image of the second set of feature portions from electrons detected by the detector emitted from the scanned feature portions in response to the scanned electron beam;

subtract the first image from the second image to generate a difference image;

when the difference image has a significantly sized defect feature that represents a difference between the first set of feature portions and the second set of feature portions and the defect feature has about a same aspect ratio as a one of the scanned feature portions, determine that the defect feature indicates an electrical defect within the scanned features; and when the difference image has a significantly sized defect feature that represents a difference between the first set of feature portions and the second set of feature portions and the defect feature has a different aspect ratio than a one of the scanned feature portions, determine that the difference feature indicates a physical defect.

13. An inspection system as recited in claim 12, wherein the features include a plurality of conductive lines, wherein the conductive lines are designed to include a plurality of lines at a grounded potential interleaved and arranged parallel with a plurality of lines at a floating potential.

14. An inspection system as recited in claim 13, wherein an electrical defect is found when two adjacent conductive lines have a same potential when scanned with the electron beam.

15. An inspection system as recited in claim 14, wherein the scanned feature portions are a plurality of end stub portions of the conductive lines.

16. An inspection system as recited in claim 15, wherein each end stub portion has a substantially same aspect ratio.

17. An inspection system as recited in claim 12, the controller further arranged to:

determine that the electrical defect is a short when the potential of the difference image is a first value; and determine that the electrical defect is a short when the potential of the difference image is a second value.

18. An inspection system as recited in claim 17, the controller further arranged to:

when an electrical defect is found, cause the electron beam to scan along the defective feature perpendicular to the first scan to form a plurality of images of portions of the defective feature not scanned in the first scan and one or more features adjacent to the defective feature;

subtract a first image of the defective feature from a second image of the defective feature to obtain a difference image, wherein the defective feature is designed to have a first portion having a bright appearance and a second portion having a dark appearance when there is an open defect present within the defective feature;

when the difference image has a significantly sized defect feature that represents a difference between the first and second image of the defective feature and the defect feature would be adjacent to a dark and bright portion of the defective feature if the difference image were overlaid with the first or second image, determine that the defect feature is an open;

when the difference image has a significantly sized defect feature that represents a difference between the first and second image of the defective feature and the defect feature would not be adjacent to a dark and bright portion of the defective feature and the defect feature touches two adjacent features if the difference image were overlaid with the first or second image, determine that the defect feature is a short defect; and when the difference image has a significantly sized defect feature that represents a difference between the first and second image of the defective feature and the defect feature would not be adjacent to a dark and bright portion of the defective feature and the defect feature does not touch two adjacent features if the difference image were overlaid with the first or second image, determine that the defect feature is a physical defect.

19. An inspection system as recited in claim 12, wherein the physical defect is selected from a group consisting of a bump in a feature edge, an uneven feature edge, an indentation in a feature edge, and a hole within an interior of the feature.

20. A computer program product for detecting defects in a plurality of features on a semiconductor device, each of the features being designed to have a particular potential when scanned with an electron beam, the computer program product comprising:

at least one computer readable medium;

computer program instructions stored within the at least one computer readable product configured to cause the inspection system to:

provide a first and second image of a first and second set of feature portions, respectively, generated as a result of scanning an electron beam over the first and second set of feature portions, wherein the first set of feature portions are designed be substantially identical to the second set of feature portions when there is no defect present;

subtract the first image from a second image to generate a difference image;

when the difference image has a significantly sized defect that represents a difference between the first set of feature portions and the second set of feature portions and the defect has about a same aspect ratio as a one of the scanned feature portions, determine that the defect indicates an electrical defect within the scanned features; and when the difference image has a significantly sized defect that represents a difference between the first set of feature portions and the second set of feature portions and the defect has a different aspect ratio than a one of the scanned feature portions, determine that the defect indicates a physical defect.

21. A method of inspecting a semiconductor device using a scanning electron microscope, the method comprising:

providing reference data;

producing scanned data by performing a voltage contrast inspection on a test structure of the semiconductor device with the scanning electron microscope;

identifying electrical defects in the test structure by comparing the scanned data with the reference data; and automatically filtering out physical defects from the electrical defects when comparing the scanned data with the reference data.

* * * * *